US010010540B2

(12) United States Patent
Henry

(10) Patent No.: US 10,010,540 B2
(45) Date of Patent: *Jul. 3, 2018

(54) AURORA A KINASE INHIBITOR

(71) Applicant: Eli Lilly and Company, Indianapolis (IN)

(72) Inventor: James Robert Henry, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/407,766

(22) Filed: Jan. 17, 2017

(65) Prior Publication Data

US 2017/0119751 A1    May 4, 2017

Related U.S. Application Data

(63) Continuation of application No. 14/934,201, filed on Nov. 6, 2015, now Pat. No. 9,637,474.

(60) Provisional application No. 62/079,742, filed on Nov. 14, 2014.

(51) Int. Cl.
   *A61K 31/4545*   (2006.01)
(52) U.S. Cl.
   CPC .............................. *A61K 31/4545* (2013.01)
(58) Field of Classification Search
   CPC .................................................. A61K 31/4545
   See application file for complete search history.

(56) References Cited

U.S. PATENT DOCUMENTS

| 8,519,136 B2 | 8/2013 | Kato |
| 9,346,787 B2 | 5/2016 | Sugimoto |

FOREIGN PATENT DOCUMENTS

| EP | 2062887 | 5/2009 |
| WO | 2008/026768 | 3/2008 |
| WO | 2009/104802 | 8/2009 |
| WO | 2013/129443 | 9/2013 |

OTHER PUBLICATIONS

Hurvitz "Triple-negative breast cancer: advancements in characterization and treatment approach" Current Opinion in Obstetrics and Gynecology 2016, 28:59-69.*
Carey L, "Triple-negative breast cancer: disease entity or title of convenience?" Nature Reviews Clinical Oncology 2010, 7, 683-92.*
Simone, Oncology: Introduction, Cecil Textbook of Medicine, 20th Edition, 1996 vol. 1, pp. 1004-1010.
Howington, "Treatment of Stage I and II Non-small Cell Lung Cancer Diagnosis and Management of Lung Cancer," 3rd ed: American College of Chest Physicians Evidence-Based Clinical Practice Guidelines CHEST 2013; 143(5) (Suppl):e278S-e313S.
Socinski "Treatment of Stage IV Non-small Cell Lung Cancer Diagnosis and Management of Lung Cancer, 3rd ed: American College of Chest Physicians Evidence-Based Clinical Practice Guideline" CHEST 2013; 143(5)(Suppl):e341S-e368S.
Jett Treatment of Small Cell Lung Cancer Diagnosis and Management of Lung Cancer, 3rd ed: American College of Chest Physicians Evidence-Based Clinical Practice Guidelines CHEST 2013; 143(5)(Suppl):e400S-e419S.
Sanz-Garcia, "Current and advancing treatments for metastatic colorectal cancer" Expert Opinion on Biological Therapy, 16:1, 2016, 93-110.
Boniface "Multidisciplinary management for esophageal and gastric cancer" Cancer Management and Research 2016:8 39-44.
Yoo "New drugs in prostate cancer" Prostate Int 4 (2016) 37-42.
Gerratana "Do platinum salts fit all triple negative breast cancers?" Cancer Treatment Reviews 48 (2016) 34-41.
Gyawali "Chemotherapy in locally advanced head and neck squamous cell carinoma " Cancer Treatment Reviews 44, 2016, 10-16.
Damia "Contemporary pre-clinical development of anticancer agents—What are the optimal preclinical models?" European Journal of Cancer 2009, 45, 2768-2781.
Sharma "Cell line-based platforms to evaluate the therapeutic efficacy of candidate anticancer agents" Nature Reviews Cancer, Apr. 2010, vol. 10, 241-253.
Ocana, A. "Preclinical development of molecular targeted agents for cancer" Nat. Rev. Clin. Oncol., 2011, 8, 200-209.
Ledford "US cancer institute overhauls cell lines" Nature, Feb. 25, 2016, vol. 530, p. 391.
Johnson, et al., "Relationships between drug activity in NCI preclinical in vitro and in vivo models and early clinical trials," British Journal of Cancer, 2001, 84, 1424-1431.
Fattaneh A. Tavassoli Peter Devilee "World Health Organization Classification of Tumours: Pathology and Genetics of Tumours of the Breast and Female Genital Organs" Online Http://www.iarc.fr/en/publications/pdfs-online/pat-gen/bb4/BB4.pdf accessed, Nov. 4, 2016 IARC Press Lyon, 2003.
HUDIS "Triple-Negative Breast Cancer: An Unmet Medical Need" The Oncologist, 2011:16 (suppl 1): 1-11.
Uscanga-Perales, G.I., et al., "Triple negative breast cancer: Deciphering the biology and heterogeneity," Medicina Universitaria, vol. 18, No. 71, pp. 105-114 (2016).
Xu, Jie, et al., "Aurora-A Identifies Early Recurrence and Poor Prognosis and Promises a Potential Therapeutic Target in Triple Negative Breast Cancer," PLOS ONE, vol. 8, No. 2: e56919 (Feb. 20, 2013). https://doi.org/10.1371/journal.pone.0056919.

* cited by examiner

*Primary Examiner* — David K O'Dell

(74) *Attorney, Agent, or Firm* — James B Myers; Elizabeth A. Dingess-Hammond; Danica Hostettler

(57) ABSTRACT

The present invention provides an aminopyridine compound, or a pharmaceutically acceptable salt thereof, that inhibits Aurora A and, therefore may be useful in treating cancer.

6 Claims, No Drawings

AURORA A KINASE INHIBITOR

The present invention relates to an aminopyridine compound, or pharmaceutically acceptable salts thereof, that inhibits Aurora A and may be useful for treating cancer.

Aurora kinases are a family of serine/threonine kinases and are key regulators of mitosis. There are three human homologs of Aurora kinases, A, B, and C, of which Aurora A has been implicated in cancers of diverse histological origin and may possess oncogenic properties when overexpressed.

Aneuploidy or genomic instability is one of the most prevalent signatures of cancer. More particularly, Aurora B inhibition induced endo-reduplication and subsequent polyploidy is one of the major pathways for genomic instability. Furthermore, the DNA endo-reduplication/polyploidy phenotype can persist for multiple cell divisions without completely killing the cancer cells. Alternatively, Aurora A selective inhibition leads to mitotic arrest in many cancer cells. The mitotic arrest often further progresses to cancer cell apoptosis or death, which is a much more desirable attribute for a cancer medicament than DNA endo-reduplication/polyploidy by Aurora B or Aurora A/B dual inhibitors. Additionally, certain Aurora B inhibitors and Aurora A/B dual inhibitors in clinical development have been reported as presenting neutropenia and bone marrow cytotoxicity in patients while certain relatively selective Aurora A inhibitors in clinical development did not show these disorders. Therefore, it is desirable to selectively inhibit Aurora A and reduce or avoid Aurora B or Aurora A/B dual inhibition. As such, selective Aurora A inhibition may be useful for cancer therapy.

Aurora A inhibitors are known in the art. WO 2008/026768, EP 2062887, and WO2009/104802 disclose certain aminopyridine compounds having Aurora A selective inhibitory action. WO 2013/129443 discloses certain piperidine compounds having Aurora A selective inhibitory activity.

There remains a need to provide alternative Aurora A inhibitors for treatment of cancer. Also, there remains a need to provide selective Aurora A inhibitors that reduce or avoid Aurora B or Aurora A/B dual inhibition. Accordingly, the present invention provides certain inhibitors of Aurora A which may be useful for treating cancer. Additionally, the present invention provides certain selective Aurora A inhibitors that may reduce Aurora B or Aurora A/B dual inhibition.

The present invention provides a compound which is 1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:

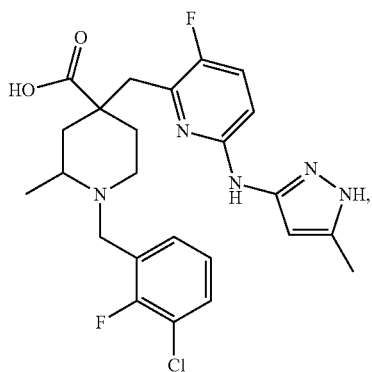

or a pharmaceutically acceptable salt thereof.

Preferably, the present invention provides a compound which is selected from the group consisting of (2S,4S)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:

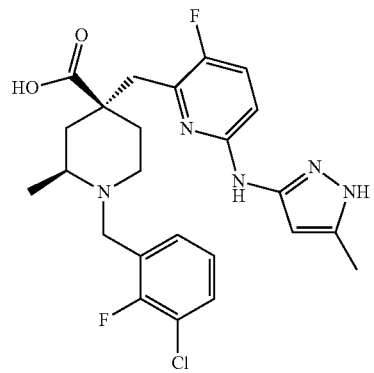

and (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:

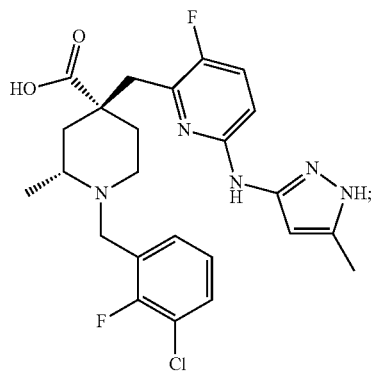

or a pharmaceutically acceptable salt thereof.

More preferably, the present invention provides a compound which is (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:

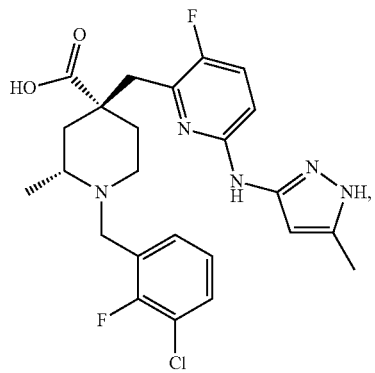

or a pharmaceutically acceptable salt thereof.

As a particular embodiment, the present invention provides the compound which is (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid.

As a particular embodiment, the present invention also provides a compound which is (2S,4S)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid.

The present invention provides a pharmaceutical composition comprising (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, or a pharmaceutically acceptable salt thereof, and a pharmaceutically acceptable carrier, diluent, or excipient. The present invention provides a pharmaceutical composition comprising (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, and a pharmaceutically acceptable carrier, diluent, or excipient.

The present invention provides a method for treating cancer comprising administering to a patient in need thereof an effective amount (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, or a pharmaceutically acceptable salt thereof. The present invention provides a method for treating cancer comprising administering to a patient in need thereof an effective amount (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid.

The present invention provides (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, or a pharmaceutically acceptable salt thereof, for use in therapy. The present invention provides (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, or a pharmaceutically acceptable salt thereof, for use in the treatment of cancer. The present invention provides a pharmaceutical composition for use in treating cancer, the pharmaceutical composition comprising (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, or a pharmaceutically acceptable salt thereof.

The present invention also provides (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid for use in therapy. The present invention provides (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid for use in the treatment of cancer. The present invention provides a pharmaceutical composition for use in treating cancer, the pharmaceutical composition comprising (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid.

The present invention provides the use of (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, or a pharmaceutically acceptable salt thereof, in the manufacture of a medicament for the treatment of cancer. The present invention also provides the use of (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid in the manufacture of a medicament for the treatment of cancer.

The present invention provides the tert-butylamine salt of (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid in a crystalline form. The present invention also provides the tert-butylamine salt of (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid in a crystalline form characterized by a X-ray powder diffraction pattern having characteristic peaks, in 2θ±0.2°, occurring at 17.0° in combination with one or more of the peaks selected from the group consisting of 11.5°, 23.2°, and 15.0°.

The present invention provides the ammonium salt of (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid in a crystalline form. The present invention also provides the ammonium salt of (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid in a crystalline form characterized by a X-ray powder diffraction pattern having characteristic peaks, in 2θ±0.2°, occurring at 4.6° in combination with one or more of the peaks selected from the group consisting of 13.8°, 17.2°, and 15.9°.

Furthermore, the present invention provides preferred embodiments of the methods and uses as described herein, in which cancer is selected from the group consisting of small cell lung cancer, colorectal cancer, gastric cancer, prostate cancer, breast cancer, triple-negative breast cancer, cervical cancer, head and neck cancer, esophageal cancer, ovarian cancer, non-small cell lung cancer, and non-Hodgkin lymphoma. Preferred cancers are small cell lung cancer, prostate cancer, triple-negative breast cancer, cervical cancer, and head and neck cancer.

The present invention also provides (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, or a pharmaceutically acceptable salt thereof, for use in simultaneous, separate or sequential administration in combination with one or more chemotherapy agents in the treatment of cancer.

As used above, and throughout the description of the invention, the following terms, unless otherwise indicated, shall be understood to have the following meanings:

A "pharmaceutically acceptable carrier, diluent, or excipient" is a medium generally accepted in the art for the delivery of biologically active agents to mammals, e.g., humans.

"Pharmaceutically acceptable salts" or "a pharmaceutically acceptable salt" refers to the relatively non-toxic, inorganic and organic salt or salts of the compound of the present invention.

"Effective amount" means the amount of the compound, or pharmaceutically acceptable salt thereof, of the present invention or pharmaceutical composition containing a compound, or pharmaceutically acceptable salt thereof, of the present invention that will elicit the biological or medical response of or desired therapeutic effect on a tissue, system, animal, mammal or human that is being sought by the researcher, veterinarian, medical doctor or other clinician.

The terms "treatment," "treat," "treating," and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

The compound of the present invention is capable of reaction, for example, with a number of inorganic and organic acids and bases to form pharmaceutically acceptable salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol 66, No. 1, January 1977.

The compound of the present invention is preferably formulated as a pharmaceutical composition using a pharmaceutically acceptable carrier, diluent, or excipient and administered by a variety of routes. Preferably, such compositions are for oral administration. Such pharmaceutical compositions and processes for preparing them are well known in the art. See, e.g., Remington: The Science and Practice of Pharmacy (A. Gennaro, et al., eds., 21st ed., Mack Publishing Co., 2005).

The amount of the compound of the present invention actually administered will be determined by a physician under the relevant circumstances, including the condition to be treated, the chosen route of administration, the actual compound of the present invention administered, the age, weight, and response of the individual patient, and the severity of the patient's symptoms. Dosages per day normally fall within the range of about 1 to about 1000 mg. In some instances, dosage levels below the lower limit of the aforesaid range may be more than adequate, while in other cases still larger doses may be employed. Dosage levels can be determined by one of skill in the art.

The compound of the present invention, or pharmaceutically acceptable salts thereof, may be prepared by a variety of procedures known in the art, as well as those described in the Preparations and Examples below. The specific synthetic steps for each of the routes described may be combined in different ways to prepare the compounds of the invention, or pharmaceutically acceptable salts thereof.

The reagents and starting materials are generally readily available to one of ordinary skill in the art. Others may be made by standard techniques of organic and heterocyclic chemistry, techniques which are known to one of ordinary skill in the art, and the procedures described in the Examples which follow including any novel procedures. The following Preparations and Examples further illustrate the invention. Unless noted to the contrary, the compounds illustrated herein are named and numbered using Accelrys Draw 4.1.

Individual isomers, enantiomers, or diastereomers may be separated or resolved by one of ordinary skill in the art at any convenient point in the synthesis of compounds by methods such as selective crystallization techniques or chiral chromatography (See, e.g., Enantiomers, Racemates, and Resolutions (J. Jacques, et al., John Wiley and Sons, Inc., 1981)).

The skilled artisan will appreciate the compound of the present invention contains at least one chiral center. More particularly, the compound of the present invention contains two chiral centers. The present invention contemplates all individual enantiomers or diastereomers, as well as mixtures of the enantiomers and diastereomers of said compounds including racemates. It is preferred that the compound of the present invention exists as a single enantiomer or diastereomer. The single enantiomer or diastereomer may be prepared beginning with chiral reagents or by stereoselective or stereospecific synthetic techniques. Alternatively, the single enantiomer or diastereomer may be isolated from mixtures by standard chiral chromatographic or crystallization techniques.

It is also known to the skilled artisan that a compound with a pyrazolyl ring can exist as a pair of tautomers in which the hydrogen can migrate between two nitrogens on the pyrazolyl ring.

The compound of the present invention can be prepared according to synthetic methods well known and appreciated in the art. Suitable reaction conditions for the steps of these reactions are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compound of the present invention is dependent upon the particular compound being synthesized, the starting compound, and the relative liability of the substituted moieties, as is well appreciated by the skilled chemist. All substituents, unless otherwise indicated, are as previously defined, and all reagents are well known and appreciated in the art.

As used herein, the following terms have the meanings indicated: "ADP" refers to adenosine 5'-diphosphate; "ATP" refers to adenosine 5'-triphosphate; "BSA" refers to bovine serum albumin; "DNA" refers to deoxyribonucleic acid; "DMSO" refers to dimethyl sulfoxide; "DTT" refers to dithiothreitol; "EDTA" refers to ethylenediaminetetraacetic acid; "EGTA" refers to ethylene glycol tetraacetic acid; "FBS" refers to fetal bovine serum; "IVTI" refers to in vivo target inhibition; "HEPES" refers to 4-(2-hydroxyethyl) piperazine-1-ethanesulfonic acid; "MEM" refers to minimum essential media; "MS" refers to mass spectroscopy; "NMR" refers to nuclear magnetic resonance; "PBS" refers to phosphate buffered saline; "MSR" refers to minimum significant ratio; "PMSF" refers to phenylmethylsulfonyl fluoride; "PNPP" refers to 4-nitrophenyl phosphate disodium salt hexahydrate; "psi" refers to pounds per square inch; "SCLC" refers to Small cell lung cancer. "TAME" refers to Nalpha-4-Tosyl-L-arginine methyl ester hydrochloride; "TED" refers to threshold effective dose; "TPCK" refers to tosyl phenylalanyl chloromethyl ketone.

PREPARATION 1

Methyl 2-methylpiperidine-4-carboxylate hydrochloride

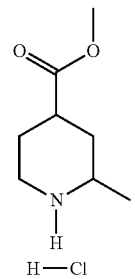

Charge PtO$_2$ (11.5 g) to a reaction vessel. Then purge the vessel with N$_2$ and wet with acetic acid (225 ml). Add methyl 2-chloro-6-methyl-pyridine-4-carboxylate (125 g) and acetic acid (1000 ml) to the slurry. Seal the reaction vessel, purge it with N$_2$, and then purge it with H$_2$ and pressurize with H$_2$. Heat the reaction mixture at 60° C. under 60 psi of hydrogen for 7 hours. Run two separate reactions under the same scale and same conditions. Filter the reaction mixture of each reaction and combine the filtrates. Concentrate the filtrates under vacuum to afford a thick oil containing some acetic acid. Add methyl tert-butyl ether (2 L) to the thick oil and stir at room temperature. Collect the resulting solids, wash with methyl tert-butyl ether (2×1000 mL) and dry under vacuum at 35° C. to provide the title compound as a white solid (400 g). $^1$H NMR (CDCl$_3$) δ 1.55 (d, J=6.3 Hz, 3H); 1.85 (q, J=12.3 Hz, 1H); 2.23-1.98 (m, 3H); 2.59-2.46 (m, 1H); 2.85 (dt, J=13.0, 3.5 Hz, 1H); 3.20-3.06 (m, 1H); 3.53 (br d, J=12.6 Hz, 1H); 3.69 (s, 3H); 9.7 (br s, 1H)

PREPARATION 2

Methyl 1-[(3-chloro-2-fluoro-phenyl)methyl]-2-methyl-piperidine-4-carboxylate

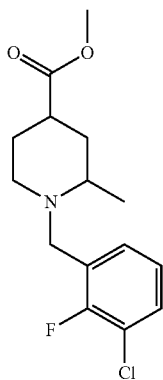

Add methyl 2-methylpiperidine-4-carboxylate hydrochloride (205.4 g, 1.06 mol), 1-(bromomethyl)-3-chloro-2-fluoro-benzene (261 g, 1.17 mol), acetonitrile (2050 mL) and potassium carbonate (293 g, 2.12 mol) to a three-necked round bottom flask (1 L). Stir the reaction mixture at reflux for 18 hours. Then stop heating, filter solids, and then rinse solids with acetonitrile (2×250 mL). Concentrate the filtrate under vacuum to give a green crude product. Dissolve in methyl tert-butyl ether (2500 ml), add CELITE®, stir then filter. Wash filtrate with water. Extract organics with 1.25N aqueous hydrochloric acid (2000 ml) then with 1M aqueous hydrochloric acid (1000 ml). Combine aqueous extracts and basify to pH ~12 with 48% aqueous sodium hydroxide (250 g). Extract with methyl tert-butyl ether (3 L). Dry organics over magnesium sulfate, filter and concentrate to give the title compound as a brown oil (272.8 g). MS (m/z): 300 (M+1).

PREPARATION 3

Methyl (2R,4R)-1-[(3-chloro-2-fluoro-phenyl)methyl]-2-methyl-piperidine-4-carboxylate

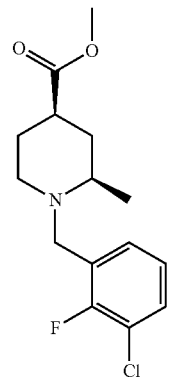 [SMILES: COC(=O)[C@@H]1CCN(Cc2cccc(Cl)c2F)[C@H](C)C1]

Separate enantiomers of methyl 1-[(3-chloro-2-fluoro-phenyl)methyl]-2-methyl-piperidine-4-carboxylate (272.8 g) using supercritical fluid chiral chromatography. Stationary phase: Chiralpak IC, mobile phase: 3% isopropyl alcohol and 0.2% dimethylethylamine Collect the first eluted enantiomer (R$_T$=1.73 min) Collect the second eluted enantiomer as the title compound (158 g, 49.7% yield; R$_T$=2.19 min; MS (m/z): 300 (M+1).). Analytical conditions: Stationary phase: Chiralpak IC, mobile phase: 5% isopropyl alcohol/0.2% isopropyl amine, flow 3 mL/min, temperature: 35° C.

PREPARATION 4

Methyl (2R,4R)-2-methylpiperidine-4-carboxylate hydrochloride

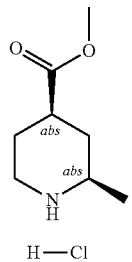

Add methyl (2R,4R)-1-[(3-chloro-2-fluoro-phenyl) methyl]-2-methyl-piperidine-4-carboxylate (250 g, 0.834 mol), 1,2-dichloroethane (1200 ml) and 1-chloroethyl chloroformate (112 ml, 1.04 mol) to a 4000 ml three neck flask. Stir at 70° C. with a mechanical stirrer for 72 hours. Add 1-chloroethyl chloroformate (30 ml, 0.227 mol) and stir at reflux for 6 hours. Allow mixture to cool to 60° C. and via an addition funnel add methanol (250 ml) over 30-45 min. Stir at 60-65° C. for 18 hours. Add methanol (400 ml) and stir at 65-68° C. for 5 hours. Allowed mixture to cool to ambient temperature and stir over night. Concentrate under vacuum to a slurry. Dilute slurry with ethyl acetate (1500 ml) and stir to 0° C. for 30 min. Collect solids and wash with ethyl acetate (1000 ml) to give the title compound as a grey solid (136.5 g, 84.5% yield). H¹ NMR (399.81 MHz, d₆-DMSO): δ 1.22 (d, J=6.5 Hz, 3H), 1.53-1.43 (m, 1H), 1.73-1.62 (m, 1H), 1.99-1.91 (m, 2H), 2.71-2.63 (m, 1H), 2.89-2.83 (m, 1H), 3.15-3.12 (m, 1H), 3.23-3.20 (m, 1H), 3.59 (s, 3H), 9.03 (br, s, 1H), 9.44 (br, s, 1H).

PREPARATION 5

O1-tert-butyl O4-methyl (2R,4R)-2-methylpiperidine-1,4-dicarboxylate

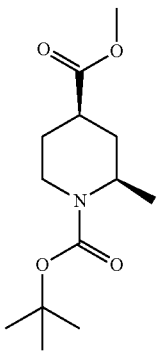 [SMILES: COC(=O)[C@@H]1CCN(C(=O)OC(C)(C)C)[C@H](C)C1]

Add methyl (2R,4R)-2-methylpiperidine-4-carboxylate hydrochloride (136 g, 0.702 mol) and dichloromethane (1500 ml) to a 4 L three neck round bottom flask equipped with an overhead stirrer. Add diisopropylethylamine (250 ml) and stir at room temperature for a few minutes. Add 4-pyridinamine-N,N-dimethyl (9.0 g, 0.74 mol). Cool in an ice/water bath. Add a solution of di-tert-butyldicarbonate (192 g, 0.88 mol) in dichloromethane (300 ml) slowly over ~30 minutes maintaining the temperature between 5-10° C. Allow the mixture to warm to room temperature and stir overnight. Add a solution of 10% oxalic acid (2 L) and stir at room temperature for 45 min. Separate the layers. Wash the organics with 5% oxalic acid (1 L). Wash organics with water then saturated NaCl, dry over sodium sulfate, filter and concentrate under vacuum. Dissolve in dichloromethane (250 ml). Apply to a silica plug (250 g) wetted with dichloromethane. Elute with dichloromethane (3 L). Concentrate the filtrate under vacuum and hold under vacuum for a few hours to give the title compound (146 g, 80.8% yield) as a pale yellow oil. H¹ NMR (399.80 MHz, CDCl₃): δ 1.05 (d, J=6.8 Hz, 3H), 1.42 (s, 9H), 1.76-1.66 (m, 1H), 1.99-1.94 (m, 3H), 2.55 (quintet, J=5.8 Hz, 1H), 3.10-3.02 (m, 1H), 3.67 (s, 3H), 3.85-3.78 (m, 1H), 4.18-4.10 (m, 1H).

PREPARATION 6

6-Bromo-2-(bromomethyl)-3-fluoro-pyridine

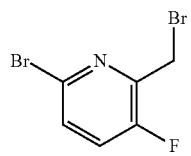

Add 6-bromo-3-fluoro-2-methyl-pyridine (50 g, 0.263 mol), N-bromosuccinimide (100 g, 0.562 mol) and carbon tetrachloride (500 ml) to a 1000 ml three neck round bottom flask equipped with a reflux condenser and nitrogen inlet. While stirring at room temperature add 2,2'-azobis(isobutyronitrile) in portions. Stir reaction for 72 hours at 78° C. Allow mixture to cool to room temperature and filter off solids. Wash solids with toluene (2×100 ml). Concentrate filtrate to ~250 ml, dilute with tetrahydrofuran (300 ml) and cool to 0-5° C. Under a nitrogen atmosphere add a solution of diethyl phosphite (37 ml, 0.288 mol) and triethylamine (40 ml, 0.287 mol) in tetrahydrofuran (100 ml) slowly over 30 min. Allow the mixture to slowly warm to room temperature over 1 hour. Concentrate under vacuum. Add ice cold water and stir until mixture is at room temperature. Collect solids and wash with water (2×200 ml). Dry the solids under vacuum. Dissolve in dichloromethane (500 ml) and filter through a plug of silica. Rinse plug with dichloromethane (250 ml). Concentrate filtrate under vacuum, dilute with hexanes (500 ml) and concentrate under vacuum to ~100 ml. Collect solids and wash with hexanes (100 ml) to obtain the title compound (48.0 g, 67.8% yield) as a white solid. Collect solids from mother liquor and dry under vacuum to obtain title compound (5.2 g, 7.35% yield) as a white solid. H¹ NMR (399.80 MHz, CDCl₃): δ 4.51 (d, J=2.1 Hz, 2H), 7.31-7.25 (m, 1H), 7.42 (dd, J=3.5, 8.6 Hz, 1H).

PREPARATION 7

O1-tert-butyl O4-methyl (2R,4R)-4-[(6-bromo-3-fluoro-2-pyridyl)methyl]-2-methyl-piperidine-1,4-dicarboxylate

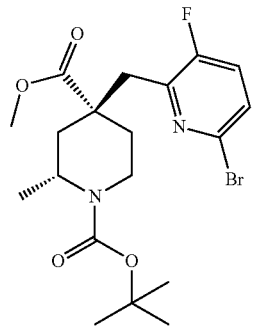 [SMILES: COC(=O)[C@]1(Cc2nc(Br)ccc2F)CCN(C(=O)OC(C)(C)C)[C@H](C)C1]

Add O1-tert-butyl-O4-methyl (2R,4R)-2-methylpiperidine-1,4-dicarboxylate (48.1 g, 0.187 mol) in tetrahyrdofuran (470 ml) to a 3 L three neck round bottom flask and cool the mixture to −78° C. Add lithium diisopropylamide (10% mass) in hexanes (112.2 ml, 0.224 mol) dropwise over 30 min maintaining the internal temperature below −71° C. Stir at −78° C. for 1.5 hours. Add a solution of 6-bromo-2-(bromomethyl)-3-fluoro-pyridine (60.4 g, 0.225 mol) in tetrahydrofuran (470 ml) dropwise over 1 hour maintaining the internal temperature below −71° C. Stir at −78° C. for 1 hour. Quench the reaction by adding a saturated aqueous ammonium chloride solution (150 ml). Collect resulting solids, dissolve in water (500 ml) and extract with ethyl acetate (1000 ml). Combine the extracts, dry over sodium sulfate, filter and concentrate under vacuum. Repeat this reaction with 57.22 g of O1-tert-butyl-O4-methyl (2R,4R)-2-methylpiperidine-1,4-dicarboxylate under same reaction condition and combine materials obtained for purification. Purify the combined material by silica gel chromatography (5-15% gradient hexanes/ethyl acetate) to obtain the title compound (168.2 g) as a light yellow oil. $H^1$ NMR (399.80 MHz, CDCl$_3$): δ 0.98 (d, J=7.1 Hz, 3H), 1.43 (s, 9H), 1.76 (dd, J=6.0, 13.8 Hz, 1H), 2.02 (s, 2H), 2.23 (dt, J=13.9, 2.1 Hz, 1H), 3.09-2.98 (m, 3H), 3.71 (s, 3H), 3.90-3.87 (m, 1H), 4.40-4.37 (m, 1H), 7.19 (t, J=8.5 Hz, 1H), 7.29 (dd, J=3.4, 8.6 Hz, 1H).

PREPARATION 8

Methyl (2R,4R)-4-[(6-bromo-3-fluoro-2-pyridyl) methyl]-1-[(3-chloro-2-fluorophenyl)methyl]-2-methyl-piperidine-4-carboxylate

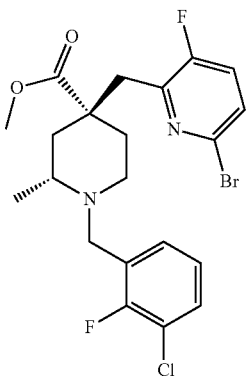 [SMILES: COC(=O)[C@]1(Cc2nc(Br)ccc2F)CCN(Cc2cccc(Cl)c2F)[C@H](C)C1]

Add O1-tert-butyl-O4-methyl (2R,4R)-4-[(6-bromo-3-fluoro-2-pyridyl)methyl]-2-methyl-piperidine-1,4-dicarboxylate (168.2 g, 0.378 mol) in 1,4-dioxane (945 ml) to a 4 L three neck round bottom flask. Add slowly over 20 minutes hydrochloric acid (4 M in 475 mL of 1,4-dioxane, 1.9 mol). Stir at room temperature for 21 hours then at 50° C. for 4 hours. Collect solids and dry under vacuum at 45° C. for 1 hour. Concentrate filtrate to a solid and dry completely. Add the combined solids, potassium carbonate (105 g, 0.76 mol) and acetonitrile (1200 ml) to a 3 L three neck round bottom flask. Stir at room temperature for 20 minutes then add 3-chloro-2-fluorobenzyl bromide (101.3 g, 0.453 mol). Stir at room temperature for 3 days. Filter the mixture through CELITE®. Concentrate the filtrate to a yellow oil. Purify the oil by silica gel chromatography (100% dichloromethane to 7% methyl-tert-butylether in dichloromethane gradient over 70 minutes) to give the title compound (153 g, 0.314 mol) as a yellow oil. MS (m/z): 489 (M+1).

PREPARATION 9

Methyl (2R,4R)-1-[(3-chloro-2-fluoro-phenyl) methyl]-4-[(3-fluoro-6-[(5-methyl-1H-pyrazol-3-yl) amino]-2-pyridyl]methyl]-2-methylpiperidine-4-carboxylate

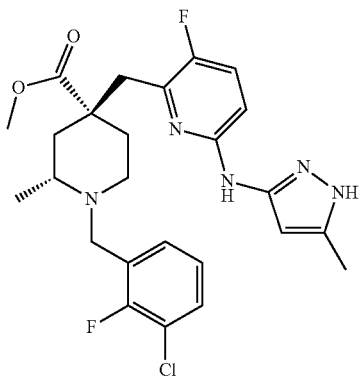

Add tert-butyl alcohol (9.4 ml) to a microwave reaction vessel and deoxygenate by nitrogen sparging for 5 minutes. Add palladium(II) acetate (0.044 g, 0.196 mmol) and 2-di-tert-butylphosphino-2',4',6'-triisopropylbiphenyl (0.251 g, 0.58 mol). Add water (0.014 ml) from underneath the surface of the solution. Heat the mixture using initiator microwave to 100° C. for 2 minutes. Add this catalyst solution via syringe to the following mixture.

Add methyl (2R,4R)-4-[(6-bromo-3-fluoro-2-pyridyl) methyl]-1-[(3-chloro-2-fluorophenyl)methyl]-2-methyl-piperidine-4-carboxylate (9.4 g, 0.019 mol), 5-methyl-1H-pyrazole-3-amine (2.07 g, 0.021 mol) and tert-butyl alcohol (65 ml) to a 3 L three neck round bottom flask. Heat the mixture to 40-45° C. and sparge with nitrogen for 10 minutes. Add cesium carbonate (14.5 g, 0.045 mol) and the catalyst solution, provided above, to the mixture. Stir at 40-45° C. for 3.5 hours. The reaction is not complete. Prepare an additional mixture of palladium(II) acetate (0.0088 g, 0.039 mmol), 2-di-tert-butylphosphino-2',4',6'-triisopropylbiphenyl (0.050 g, 0.103 mmol), water (2.8 μL) and tert-butyl alcohol (2 ml). Heat this mixture using initiator microwave to 100° C. for 2 min and then add it to the above incomplete reaction mixture. Stir the reaction mixture at 40-45° C. for 2 hours. Dilute the mixture with ethyl acetate (100 mL), filter through a CELITE® plug and wash plug with ethyl acetate (100 mL). Concentrate under vacuum. Repeat the reaction with 129.35 g of methyl (2R,4R)-4-[(6-bromo-3-fluoro-2-pyridyl)methyl]-1-[(3-chloro-2-fluorophenyl) methyl]-2-methyl-piperidine-4-carboxylate under the same reaction condition as describe above and combine the crude materials for purification.

Combine the two crude reaction products. Purify the material by silica gel chromatography 30% ethyl acetate in 1:1 dichloromethane/hexanes to 100% ethyl acetate to obtain 95 g of a pink solid. Add the solid to a 4 L flask with SILIAMETS® THIOL (120 g) and dichloromethane (2 L). Stir at room temperature overnight. Filter the mixture through CELITE®. Concentrate the filtrate to dryness to give the title compound (93.3 g) as a white foam. MS (m/z): 504 (M+1).

EXAMPLE 1

(2R,4R)-1-[(3-Chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid

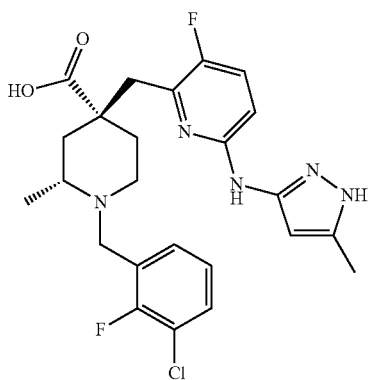

Add methyl (2R,4R)-1-[(3-chloro-2-fluoro-phenyl) methyl]-4-[3-fluoro-6-[(5-methyl-1H-pyrazol-3-yl)amino]-2-pyridyl]methyl]-2-methylpiperidine-4-carboxylate (19.95 g, 0.040 mol), hydrochloric acid (36.5% mass) and water (140 ml, 1.63 mol) to a 1 L three neck round bottom flask. Stir at 93-96° C. for 17 hours. Cool to room temperature and concentrate under vacuum. Dissolve residue in water (1000 ml) and cool in an ice bath. Adjust pH to 6.5 with 5N sodium hydroxide. Collect the resulting solids and wash with water. Extract the aqueous filtrate with 10% isopropanol/dichloromethane (3×500 ml). Dry and concentrate to a solid. Combine both solids and dissolve in ethanol (200 ml). Dilute with ethyl acetate (1500 ml) and stir at room temp overnight. Filter and concentrate under vacuum to a solid. Dissolve solids in 5% methanol/dichloromethane, dilute with ethyl acetate (500 ml) and concentrate to 300 ml. Filter off solids. Repeat the reaction with 61.9 g of methyl (2R,4R)-1-[(3-chloro-2-fluoro-phenyl)methyl]-4-[(3-fluoro-6-[(5-methyl-1H-pyrazol-3-yl)amino]-2-pyridyl)methyl]-2-methylpiperidine-4-carboxylate under the same reaction condition as described above. Combine filtrates from both reactions. Concentrate the combined filtrates to ~600 ml and dilute with hexanes (600 ml). Collect solids and dry under vacuum at 50° C. overnight. Concentrate mother liquors under vacuum to dryness and dry solids under vacuum at 50° C. overnight. Combine solids to give the title compound (63.44 g). MS (m/z): 490 (M+1). $[\alpha]^{20}_D$ +17.3° (c 1.00, EtOH).

EXAMPLE 2 tert-Butylamine salt of (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid

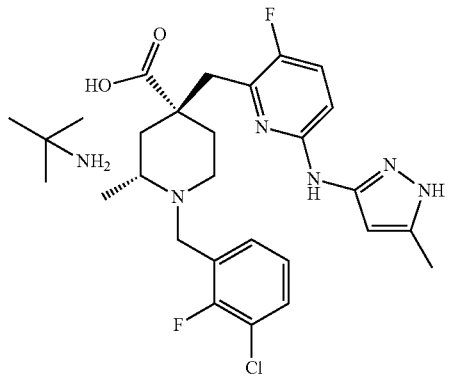

Add (2R,4R)-1-[(3-chloro-2-fluoro-phenyl)methyl]-4-[[3-fluoro-6-[(5-methyl-1H-pyrazol-3-yl)amino]-2-pyridyl] methyl]-2-methyl-piperidine-4-carboxylic acid (580 mg) in 4 mL of acetone. The solid dissolves to form a clear yellow solution while stirring at 60° C. (plate temperature)/1000 rpm. Add tert-butylamine (150 µL, 1.20 equivalents, 99.5%) to the solution and the precipitation is observed. Slurry the mixture for another 10 minutes at 60° C. and then allow it to cool to room temperature. Filter the solid by vacuum filtration and dry the solid in a vacuum oven at 60° C. to provide the title compound (635 mg, 95.26% yield).

EXAMPLE 3

Ammonium salt of (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid

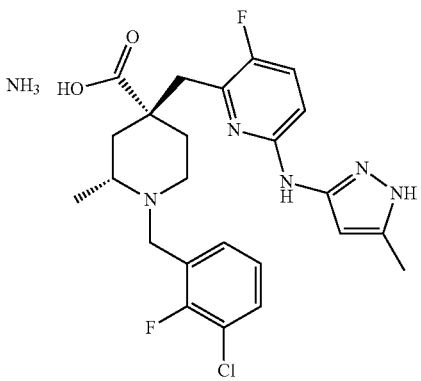

Add (2R,4R)-1-[(3-chloro-2-fluoro-phenyl)methyl]-4-[[3-fluoro-6-[(5-methyl-1H-pyrazol-3-yl)amino]-2-pyridyl] methyl]-2-methyl-piperidine-4-carboxylic acid (154 mg) in 2 mL of acetone. The solid dissolves to a clear yellow solution while stirring at 60° C. (plate temperature)/1000 rpm. Add ammonium hydroxide (29.8%, 50 µL, 1.22 equivalents) to the solution and the precipitation is observed. Slurry the mixture for another two hours at 60° C. and then allow it to cool to room temperature. A thick slurry of bright white solid is observed. Filter the solid by vacuum filtration and dry the solid in a vacuum oven at 60° C. to provide the title compound (145 mg, 90.81% yield).

X-Ray Powder Diffraction of Examples 2 and 3

The XRD patterns of crystalline solids are obtained on a Bruker D4 Endeavor X-ray powder diffractometer, equipped with a CuKa source λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.853 and 26.774 degrees 2-theta.

A prepared sample of Example 2 is characterized by an XRD pattern using CuKa radiation as having diffraction peaks (2-theta values) as described in Table 1 below, and in particular having peaks at 17.0° in combination with one or more of the peaks selected from the group consisting of 11.5°, 23.2°, and 15.0°; with a tolerance for the diffraction angles of 0.2 degrees.

TABLE 1

X-ray powder diffraction peaks of Example 2

| Peak | Angle (°2-Theta) +/− 0.2° | Relative Intensity (% of most intense peak) |
|---|---|---|
| 1 | 8.0 | 24.6 |
| 2 | 11.5 | 57.1 |
| 3 | 14.0 | 26.4 |
| 4 | 15.0 | 42.3 |
| 5 | 17.0 | 100.0 |
| 6 | 19.3 | 24.9 |
| 7 | 21.0 | 37.1 |
| 8 | 23.2 | 45.1 |
| 9 | 24.0 | 30.9 |
| 10 | 26.1 | 23.7 |

A prepared sample of Example 3 is characterized by an XRD pattern using CuKa radiation as having diffraction peaks (2-theta values) as described in Table 2 below, and in particular having peaks at 4.6° in combination with one or more of the peaks selected from the group consisting of 13.8°, 17.2°, and 15.9°; with a tolerance for the diffraction angles of 0.2 degrees.

TABLE 2

X-ray powder diffraction peaks of Example 3

| Peak | Angle (°2-Theta) +/− 0.2° | Relative Intensity (% of most intense peak) |
|---|---|---|
| 1 | 4.6 | 100.0 |
| 2 | 9.3 | 38.1 |
| 3 | 9.9 | 26.1 |
| 4 | 10.5 | 39.4 |
| 5 | 13.8 | 72.2 |
| 6 | 15.9 | 62.7 |
| 7 | 17.2 | 66.6 |
| 8 | 18.5 | 40.3 |
| 9 | 21.3 | 52.3 |
| 10 | 28.1 | 49.8 |

X-Ray Crystal Structure of Aurora A Kinase Using Example 3

The catalytic domain of Aurora A kinase (residues 125-391 of sequence NP_003591) is expressed in Sf9 insect cells with a TEV protease cleavable N-terminal poly-Histidine tag. The expressed protein is isolated by binding to a nickel chelating column After cleavage of the histidine tag, the protein is further purified by passing over a size-exclusion chromatography column (16/600 S200; GE Lifesciences) equilibrated in a buffer containing 50 mM sodium phosphate pH 7.0, 250 mM NaCl, 1 mM EDTA, 5 mM DTT, and 0.1 mM with β,γ-imidoadenosine 5'-triphosphate (AMP-PNP). The purified Aurora A kinase protein at a concentration of 8.3 mg/ml is supplemented with additional AMP-PNP to a final concentration of 2 mM, and crystallized at 21° C. by vapor diffusion. Crystallization is performed by mixing 0.8 μL of protein with 0.8 μL of reservoir solution containing 100 mM MES pH 4.6, 23% PEG 3350 and 150 mM ammonium sulfate, and equilibrating against the same reservoir in sitting drop trays. A single crystal of Aurora A kinase in complex with AMP-PNP is soaked overnight in a solution containing 2 mM of Example 3, and transferred to a solution containing 20% Polyethylene glycol 400, and flash frozen in liquid nitrogen. X-Ray diffraction data to 1.96 Å is collected from the frozen crystal at the Lilly Research Laboratories Collaborative Access Team Beam-Line (LRL-CAT APS 3 HD) at the Advanced Photon Source, Argonne, Ill. X-rays of wavelength 0.9793 Å are used to collect 180 frames in 1° oscillations, with a detector distance of 185 mm. The structure of Aurora A kinase using Example 3 is determined by Molecular Replacement and refined to a R-factor of 20.6% and a R-free of 25.6%. The result is with Example 3 and provides the stereochemistry. It also provides stereochemistry for Examples 1 and 2 since Example 1 is used as a starting material for the preparation of Examples 2 and 3.

TABLE 3

Atomic coordinates of ligand in complex resulting from
the treatment of Aurora A crystals with Example 3

| ATOM | X | Y | Z | B-Factor |
|---|---|---|---|---|
| C1 | 112.063 | −22.352 | 4.479 | 42.62 |
| C2 | 112.093 | −21.548 | 5.620 | 40.92 |
| C3 | 106.478 | −13.876 | 6.709 | 30.97 |
| C4 | 112.494 | −21.851 | 3.250 | 39.63 |
| C5 | 106.509 | −14.173 | 5.352 | 32.26 |
| C6 | 109.743 | −16.303 | 3.016 | 23.86 |
| C7 | 112.557 | −20.234 | 5.530 | 49.20 |
| C8 | 107.454 | −14.403 | 7.543 | 30.71 |
| C9 | 112.992 | −19.735 | 4.307 | 46.02 |
| C10 | 112.961 | −20.539 | 3.170 | 49.13 |
| C11 | 108.433 | −15.216 | 6.985 | 29.52 |
| C12 | 110.350 | −16.658 | 1.793 | 21.45 |
| C13 | 107.527 | −15.000 | 4.893 | 27.64 |
| C14 | 108.526 | −15.780 | 2.647 | 22.41 |
| C15 | 107.800 | −17.220 | 8.960 | 40.44 |
| C16 | 109.027 | −18.128 | 6.966 | 34.87 |
| C17 | 110.137 | −17.883 | 9.201 | 32.43 |
| C18 | 110.391 | −18.481 | 6.358 | 28.24 |
| C19 | 111.482 | −18.224 | 8.537 | 32.71 |
| C20 | 109.128 | −17.256 | 8.229 | 32.98 |
| C21 | 111.684 | −17.267 | 1.564 | 24.45 |
| C22 | 112.398 | −18.885 | 9.578 | 37.45 |
| C23 | 112.608 | −19.345 | 6.737 | 32.82 |
| C24 | 109.500 | −15.812 | 7.858 | 33.06 |
| N25 | 108.492 | −15.529 | 5.670 | 28.42 |
| N26 | 108.483 | −15.845 | 1.290 | 23.85 |
| N27 | 109.585 | −16.379 | 0.739 | 22.58 |
| N28 | 111.302 | −19.083 | 7.346 | 32.56 |
| N29 | 107.540 | −15.286 | 3.509 | 30.18 |
| O30 | 106.690 | −17.266 | 8.449 | 39.38 |
| O31 | 108.001 | −17.113 | 10.295 | 42.47 |
| F32 | 107.438 | −14.126 | 8.849 | 36.03 |
| F33 | 113.435 | −18.468 | 4.239 | 56.09 |
| CL34 | 113.500 | −19.908 | 1.663 | 70.06 |

The results of the following assays demonstrate that the compound of Example 1 of the present invention is an Aurora A inhibitor. Additionally, the results of the following assays demonstrate that the compound of Example 1 is a selective Aurora A inhibitor that may reduce Aurora B or Aurora A/B dual inhibition. Also, the results of the following assays demonstrate that the compound of Example 1 induces cell cycle mitotic arrest by inhibition of Aurora A kinase activity. Additionally, the compound of Example 1 demonstrates Aurora A, not Aurora B, kinase target inhibition in vivo with xenograft tumor samples, as well as significant anti-tumor growth efficacy in the small cell lung cancer NCI-H446 nude mice model.

Aurora A Kinase Assay

This assay measures the ability of testing compounds to inhibit Aurora A kinase activity in vitro by TRAN-SCREENER® ADP-Fluorescent Polarization measurement in a 96 black well plate format (CORNING® COSTAR® 3694). Prepare a solution in a kinase buffer [50 mM 4-(2-hydroxyethyl)-1-piperazineethanesulfonic acid (HEPES) pH 7.4, 4 mM $MgCl_2$, 0.01% TRITON™ X-100 and 2 mM dithiothreitol (DTT)] with adenosine triphosphate (ATP) and Aurora A kinase activation loop (ENOGEN®, #326861) at final concentrations of 20 μM ATP and 150 μM Aurora A kinase activation loop, respectively. The Aurora A enzyme is added to the solution with a final concentration of 0.096 ng/μL. Testing compounds are serially diluted 1:3 in 20% dimethyl sulfoxide (DMSO) to create a 10 point dose response curve at the final concentrations starting at 20 μM. DMSO buffer alone without testing compound is used as positive control (full Aurora A activity in the absence of inhibitor). The negative control is a full reaction mixture plus 100 nM of ethylenediaminetetraacetic acid (EDTA) to determine the adenosine 5'-diphosphate (ADP) background level. Add the prepared Aurora A enzyme solution to the plate containing testing compounds and the positive and negative controls and pre-incubate the mixture for 30 minutes at 22° C. The reaction is started by adding ATP and Aurora A kinase activation loop solution and lasts for 30 minutes at 22° C. The reaction is then stopped by adding 25 μL (1:1 v:v) of ADP detection mixture containing ADP far red tracer, ADP antibody and the Stop and Detection buffer (Bellbrook Labs cat #3003-10K). The plates are kept in the dark for at least 2 hours to allow the displacement of ADP Alexa633 Tracer (bound to ADP2 Antibody) by ADP produced in the kinase reaction, and the decrease in fluorescence polarization is determined (Ultra384, Tecan). A standard curve of ADP/ATP in the above kinase buffer is used to determine ADP conversion for the test compounds.

The difference between the median value of positive and negative controls is taken as 100% activity. A four parameter logistic curve fit is used to generate the $IC_{50}$ values using ActivityBase™ software (IDBS, Alameda Calif.). The assay displays a Minimum Significant Ratio (MSR) of ≤3.

A compound within the scope of the invention is tested in this assay substantially as described above. The compound of Example 1 is determined to have an $IC_{50}$ of 1.12±0.15 nM (n=4). The Aurora A biochemical assay reaches the assay low detection limit such that the reported $IC_{50}$ may not reflect the absolute compound inhibition potency in vitro; however, the assay itself is statistically validated so that this data provides the $IC_{50}$ result the compound demonstrates in the assay. Therefore, the results show that Example 1 inhibits Aurora A kinase activity in vitro.

Aurora B Kinase Assay

This assay measures the ability of testing compounds to inhibit Aurora B kinase activity in vitro by TRAN-SCREENER ADP-Fluorescent Polarization measurement in a 96 black well plate format (CORNING COSTAR 3694). Prepare a Aurora B enzyme solution in a kinase buffer (37.5 mM HEPES pH 7.4, 6.25 mM $MgCl_2$, 0.0075% TRITON™ X-100 and 2.5 mM DTT) with Aurora B enzyme (final concentrations of 0.39 ng/μL), 0.1 μM INCEP peptide (GenScript, #92480_1, final concentrations 0.1 μM), ATP (final concentration 10 μM), and Histone H3 (Anaspec, #KLH08-4, final concentration 5 μM). Testing compounds are serially diluted 1:3 in 20% DMSO to create a 10 point dose response curve at the final concentrations starting at 20 μM. DMSO buffer alone without compound is used as positive control (full Aurora B activity in the absence of inhibitor). The negative control is the full reaction mixture plus 100 nM EDTA to determine the ADP background level. Add the prepared Aurora B enzyme solution to the plate containing testing compounds and the positive and negative controls. Pre-incubate the mixture for 30 minutes at 22° C. The above ATP and Histone H3 solutions are added to start the reaction and the plate is incubated for 45 minutes at 22° C. The reaction is stopped by adding 25 μL (1:1 v:v) of ADP detection mixture containing ADP far red tracer, ADP antibody and stop and detection buffer (Bellbrook Labs cat #3003-10K). The plates are kept in the dark for at least 2 hours to allow the displacement of ADP Alexa633 Tracer (bound to ADP2 Antibody) by ADP produced in the kinase reaction before fluorescent polarization is determined (Ultra384, Tecan). A standard curve of ADP/ATP in kinase buffer described above is established to determine ADP conversion for the test compound.

The difference between the median value of positive and negative control is taken as 100% activity. A four parameter logistic curve fit is used to generate the $IC_{50}$ values using ActivityBase™ software (IDBS, Alameda Calif.). The assay displays a Minimum Significant Ratio (MSR) of ≤3.

A compound within the scope of the invention is tested in this assay substantially as described above. The compound of Example 1 is determined to have an $IC_{50}$ of 1510±668 nM (n=5). The results show that Example 1 inhibits Aurora B kinase activity in vitro less than it inhibits Aurora A kinase activity in vitro.

Histone H3 Phospho-Ser10 and DNA Content Cell Based Phenotypic Multiplexing Assay The assay measures Aurora A inhibition induced mitotic arrest. The Aurora A inhibition induced mitotic arrest is measured with mitotic marker histone H3 phospho-Ser10 increase, 4N (G2/M) DNA content increase, and cell proliferation inhibition phenotypes with 24-hour compound treatment using Acumen Explorer™ (Laser-scanning fluorescence microplate cytometer (TTP LabTech LTD, UK)). Hela cells from the American Type Culture Collection (ATCC) are plated at 5000 cells/well in 96 well BD BIOCOAT™ poly-D-lysine plates (Becton Dickinson, catalog #356640) and are incubated at 37° C. for 24 hours under 5% $CO_2$ in Minimum Essential Media (MEM) (e.g. Gibco, catalog #31095) with 10% Fetal Bovine Serum (FBS) (e.g. Gibco, catalog #16000), 1% nonessential amino acids (e.g. Gibco, catalog #11140), 1% sodium pyruvate (e.g. Gibco catalog #11360) and 1% Penicillin-Streptomycin (e.g. Gibco, catalog #15140). Cells are treated by adding testing compounds to the medium, dosing at 10 points of 1:3 serial dilutions across the range of 20 μM to 0.001 μM, and with final DMSO concentration of 0.25%. After 24 hours of exposure to the compounds, cells are fixed with PREFER™ (Anatech LTD., catalog #414) for 30 minutes at room temperature, washed once with phosphate buffered saline (PBS) and permeabilized with 0.1% TRITON® X100 in PBS solution for 15 minutes at room temperature. Cells are washed twice with PBS and blocked with 1% bovine serum albumin (BSA) in PBS (e.g. Sigma, catalog # A7030) for 30 minutes at room temperature. The primary anti-histone H3 phospho-Ser10 rabbit polyclonal antibody (Millipore, catalog #06-570) is added at 1:1000 in PBS with 1% BSA to the cells and incubated over night at 4° C. After two washes with PBS, cells are incubated with goat anti-rabbit IgG Alexa 488 labeled secondary antibody 1:1000 in PBS (Invitrogen cat # A11008) for 1 hour at room temperature. After two more washes with PBS, a solution containing 10 μg/mL propidium iodide (Invitrogen catalog # P3566) and 50 μg/mL Ribonuclease A (Sigma catalog # R-6513) in PBS is added to stain nuclei. Fluorescence plates are scanned with ACUMEN EXPLORER™ [Laser-scanning fluorescence microplate cytometer (comprising 488 nm argon ion laser excitation and multiple photomultiplier tube detection, manufactured by TTP LabTech Ltd.) to measure histone H3 phospho-Ser10 and DNA content Image analysis is based on cellular fluorescent signals to identify cells in different subpopulations. Assay outputs are percentage of cell proliferation inhibition, percentage of histone H3 phospho-Ser10 positive cells, percentage of 2N (G1 cell cycle or diploid DNA content where N refers to a single complement of chromosomes, the haploid DNA content) and the percentage of 4N plus >4N (G2/M cell cycle and beyond) of DNA histogram profiles. The $IC_{50}$ and $EC_{50}$ values are determined by curve fitting to a four parameter logistic for each output using ACTIVITY BASE™.

A compound within the scope of the invention is tested in this assay substantially as described above. The compound of Example 1 shows mitotic arrest with $EC_{50}$ of 108±15 nM (n=4) for increase of Histone H3 P-Ser10, $EC_{50}$ of 108±27 nM (n=4) for 4N-DNA content increase, and $IC_{50}$ of 52.9±27 nM (n=4) for cell proliferation inhibition, respectively.

Aurora B Histone H3 Phospho-Ser10 Inhibition Cell Based Assay

The assay measures the Aurora B inhibition induced histone H3 phospho-Ser10 decrease with one hour of testing compound treatment. NCI-H446 cells from the American Type Culture Collection (ATCC) are plated at 12000 cells/well in 96 well BD BIOCOAT™ poly-D-lysine plates (Becton Dickinson, catalog #356640) and are incubated at 37° C. for 24 hours under 5% $CO_2$ in Roswell Park Memorial Institute (RPMI) medium (e.g. Gibco, catalog #52400) with addition of 10% FBS (e.g. Gibco, catalog #16000) and 1% Penicillin-Streptomycin (e.g. Gibco, catalog #15140). Cells are treated by adding testing compounds to the medium, dosing at 10 points of 1:3 serial dilutions across the range of 40 μM to 0.002 μM, with final DMSO concentration of 0.2%. After one hour of exposure to the testing compounds, cells are fixed with 16% formaldehyde in PBS (final concentration 4% from a stock of Formaldehyde 37% Solution, Sigma catalog # F1635) for 45 minutes at room temperature, washed once with PBS and permeabilized with cold methanol for 15 minutes at room temperature. Then cells are washed once with 0.1% TRITON® X100 in PBS solution, twice with PBS and blocked with 3% Skim Milk in PBS (Difco, catalog #232100) for 30 minutes at room temperature. The primary anti-histone H3 phospho-Ser10 rabbit polyclonal antibody (Millipore, catalog #06-570) is added at 1:1000 in 3% Skim Milk in PBS to the cells and incubated over night at 4° C. After washing once with 0.1% TRITON® X100 in PBS solution and twice with PBS, cells are incubated with goat anti rabbit IgG Alexa 488 labeled secondary antibody 1:1000 in PBS (Invitrogen cat # A11008) for one hour at room temperature. After two more washes with PBS, a solution containing 10 μg/mL propidium iodide (Invitrogen catalog # P3566) and 50 μg/mL Ribonuclease A (Sigma catalog # R-6513) in PBS is added to stain nuclei. Fluorescence plates are scanned with ACUMEN EXPLORER™ [Laser-scanning fluorescence microplate cytometer (comprising of 488 nm argon ion laser excitation and multiple photomultiplier tube detection, manufactured by TTP LABTECH LTD) to measure phosphorylation of Histone H3 protein and DNA content. Image analysis is based on cellular fluorescent signals to identify cells in different subpopulations. Assay output is percentage of Histone H3 phospho-Ser10 positive cells. The $IC_{50}$ values are determined by curve fitting to a four parameter logistic for each output using Genedata Screener®.

A compound within the scope of the invention is tested in this assay substantially as described above. The compound of Example 1 shows Aurora B inhibition $IC_{50}$ at 1467±456 nM (n=4). Taken together with the Aurora A phosphor-Thr288 MSD cell based assay data, provided herein below, Example 1 shows selectivity for Aurora A over Aurora B.

Cell Lysates and Histone Extraction Preparation

This is the protocol to prepare the cell lysate supernatants to be used for the following ELISA Meso Scale Discovery (MSD) Aurora A phosphorylation inhibition assay. Small cell lung cancer (SCLC) H446 cell lysate is prepared according to MSD manufacturer specifications (http://www.mesoscale.com/CatalogSystemWeb/Documents/Phospho_Aurora_A_Thr288_WCL.pdf) using lysis buffer (Tris 25 mM, pH 7.5; Leupeptin 10 µg/mL; Trypsin-Chymotrypsin 10 µg/mL; tosyl phenylalanyl chloromethyl ketone (TPCK) 10 µg/mL; Aprotinin 10 µg/mL; β-glycerophosphate 60 mM; Triton X-100 1%; Sodium pyrophosphate ($Na_2H_2P_2O_7$) 2.5 mM; NaCl 150 mM; EDTA 15 mM; ethylene glycol tetraacetic acid (EGTA) 5 mM; Nalpha-4-Tosyl-L-arginine methyl ester hydrochloride (TAME) 2 mM; 4-nitrophenyl phosphate disodium salt hexahydrate (PNPP) 15 mM; benzamidine 5 mM; sodium vanadate 1 mM; sodium fluoride 10 mM; phenylmethanesulfonylfluoride (PMSF) 50 µg/mL; DTT 1 mM; okadaic acid 1 µM; Microcystine 1 µM). The supernatant protein concentration is measured by Biorad DC-Protein assay (#500-0111, BioRad) and 25 µL of 1 mg/mL cell lysate is used for Aurora A phosphor-Thr288 MSD assay.

Aurora A Phosphor-Thr288 MSD Cell Based Assay

The purpose of the assay is to measure the Aurora A kinase inhibition activity in cell culture. The assay is performed using 96-well ELISA Meso Scale Discovery (MSD) plates (#K150 JCD Whole Cell Lysate Kit, Meso Scale Discovery, Md.).

A MULTI-SPOT® Phospho-Aurora A Singleplex plate is blocked with 150 µL/well of Blocking Solution-A (final concentration 3% BSA). Shake the plate at room temp for 1 hour and washing with MSD TrisWash Buffer three times. Dispense 25 µL of 1 mg/mL cell lysates into MULTI-SPOT® Phospho-Aurora MSD plate. Incubate the mixture for additional 3 hours at room temperature and wash the mixture with MSD TrisWash buffer three times. Detection antibody (SULFO-TAG™ anti-AuroraA Phospho-T288) is diluted 50× in 1% BSA antibody dilution buffer (1 part of 3% BSA with 2 parts of MSD washing buffer; 0.02% of blocker D-R), and 25 µl/well is added into the plate with shaking for 1 hour at room temperature. The plate is washed 3 times with MSD TrisWash Buffer before 150 µL/well 2×MSD Read Buffer T is added into the plate and plates is read on a MSD SECTOR™ Imager 6000 instrument. Percentage of inhibition is defined as [(100−(MSD value−MSD maximum inhibition value)/(MSD minimum inhibition value−MSD maximum inhibition value)]*100. The "maximum" and "minimum" are defined by 2 µM positive control compound alisertib vs. DMSO negative control alone.

A compound within the scope of the invention is tested in this assay substantially as described above. The compound Example 1 shows Aurora A inhibition with 1 hour compound treatment in the cell with an $IC_{50}$ at 1.4±1.1 nM (n=2). The data shows that Example 1 demonstrates Aurora A kinase inhibition activity in cell culture.

Tumor Protein Lysate and Histone Extraction Preparation

This is the protocol to prepare the xenograft tumor lysates and histone extract used in the following in vivo target inhibition (IVTI) assays. Tumor samples are chilled in liquid nitrogen and placed on foil sheets and the mortar and pestle on a dry ice container. The tumor tissue samples are ground with pestle and the pulverized tumor tissues are transferred to a tube containing Lysing Maxtrix D beads (#6913-500; Biomedicals MP Lysing Maxtrix D) and 0.6 mL of lysis buffer (Tris 25 mM, pH 7.5; Leupeptin 10 µg/mL; Trypsin-Chymotrypsin 10 µg/mL; TPCK 10 µg/mL; Aprotinin 10 µg/mL; β-glycerophosphate 60 mM; Triton X-100 1%; sodium pyrophosphate ($Na_2H_2P_2O_7$) 2.5 mM; NaCl 150 mM; EDTA 15 mM; EGTA 5 mM; Nalpha-4-Tosyl-L-arginine methyl ester hydrochloride (TAME) 2 mM; PNPP 15 mM; benzamidine 5 mM; sodium vanadate 1 mM; sodium fluoride 10 mM; PMSF 50 µg/mL; DTT 1 mM; okadaic acid 1 µM; microcystine 1 µM) plus complete EDTA free tablet (#1873580; Roche). The tubes are shaken vigorously for 30 seconds at speed 6.0 in Bio101 fastPrep (#Bio 101; Thermo Seweant). The tumor lysate is prepared according to MSD manufacturer specifications (http://www.meso-scale.com/CatalogSystemWeb/Documents/Phospho_Aurora_A_Thr288_WCL.pdf). The supernatant protein concentration is determined by the Biorad DC-Protein assay (#500-0111).

Total Histone extraction kit (#OP-0006; EpiQuik) is used to extract total histone from the tumor tissue pellet in the above centrifuge step according to manufactures specifications (http://www.epigentek.com/docs/OP-0006.pdf). The protein concentration is measured by Biorad DC-Protein assay (#500-0111; BioRad), and 25 µL, of 0.25 mg/mL histone extract protein is used for IVTI histone H3 phospho-Ser10 assays.

Aurora A In Vivo Target Inhibition (IVTI) Phosphor-Thr288 MSD Assay

The purpose of the assay is to measure the Aurora A kinase inhibition in vivo with xenograft tumor samples. Perform the assay with a 96-well ELISA Meso Scale Discovery (MSD) plate format. A MULTI-SPOT® Phospho-Aurora A Singleplex plate (K150 JCD Whole Cell Lysate Kit; Meso Scale Discovery, Md.) is charged with 150 µL/well of Blocking Solution-A (final concentration 3% BSA). Shake the plate at room temp for 1 hour and wash with TrisWash Buffer three times. Tumor lysates are prepared from above tumor lysate protocol to 1 mg/mL and 25 µL/well is dispensed into MULTI-SPOT® Phospho-Aurora MSD plate. Incubate the mixture for additional 3 hours at room temperature, and wash 3 times with TrisWash buffer washing. Detection SULFO-TAG™ anti-AuroraA Phospho-T288 antibody in 1% BSA antibody dilution buffer (antibody diluted 50× into the buffer with 1 part of 3% BSA plus 2 parts of washing buffer; 0.02% of blocker D-R) in the amount of 25 µL/well is added into the plate and shake the plate for 1 hour at room temperature. Wash the plate 3 times with TrisWash Buffer, add 150 µL/well 2× Read Buffer T into the plate, and then read immediately on a MSD SECTOR™ Imager 6000 instrument. The percentage of inhibition is defined as [100−(compound treatment group mean MSD reading/vehicle group mean MSD reading)]*100.

A compound within the scope of the invention is tested in this assay substantially as described above. The compound of Example 1 shows $TED_{50}$ of 2.13 mg/kg with H446 xenograft model in nude mice (Threshold Effective Dose) in a dose response study 3 hours post dosing. The data shows that Example 1 demonstrates Aurora A kinase inhibition in vivo with xenograft tumor samples at the specified TED.

Aurora B In Vivo Target Inhibition (IVTI) Histone H3 Phospho-Ser10 MSD Assay

The purpose of the assay is to measure the Aurora B kinase inhibition activity in vivo with xenograft tumor samples by determine the histone H3 phospho-Ser10 inhibition since it is a direct downstream kinase substrata of Aurora B. Perform the assay with a 96-well ELISA Meso Scale Discovery (MSD) plate format. Blocking Solution-A (final concentration 3% BSA) is added to a MULTI-SPOT® Histone H3 4-Spot plate (Cat# K150 EWD-3 JCD Whole Cell Lysate Kit, Meso Scale Discovery, Md.) at 150 μL/well and shake the plate at room temperature for 1 hour. After washing 3 times with MSD TrisWash Buffer, histone extract prepared to 0.25 mg/mL with above tumor lysate protocol is dispensed onto the MSD plate at 25 μL/well. Incubate the mixture for additional 3 hours at room temperature, wash 3 times with MSD TrisWash buffer. Detection SULFO-TAG anti-histone H3 phospho-Ser10 antibody is diluted 50× into 3 mL 1% BSA antibody dilution buffer (1 ml 3% BSA with 2 mL MSD washing buffer; 0.01% of blocker D-M), and 25 μL/well is added into the plate and shake the plate at room temperature for 1 hour. Plate is then washed 3 times with MSD TrisWash Buffer. Add 150 μL/well of 2×MSD Read Buffer T to the plate. Read the plate immediately with a MSD SECTOR™ Imager 6000 instrument. The percentage of inhibition is defined as [100−(compound treatment group mean MSD reading/vehicle group mean MSD reading)]*100.

A compound within the scope of the invention is tested in this assay substantially as described above. The compound of Example 1 does not provide over 50% histone H3 phospho-Ser10 inhibition in the assay in a dose response study at 30 mg/kg 3 hours post dosing, and in a time course study at 50 mg/kg 1 hour post dosing. The result suggests that Example 1 does not inhibit Aurora B in vivo with xenograft tumor samples at the specified doses.

Anti-Tumor Growth Efficacy with SCLC NCI-H446 Nude Mice Xenograft Model

The assay is to measure the in vivo tumor growth inhibition in SCLC NCI-H446 and SCLC NCI-H69 nude mice xenograft models. All in vivo studies are performed according to the Institutional Animal Care and Use Protocols. For xenograft models, human small cell lung cancer NCI-H446 cells and human small cell lung cancer NCI-H69 cells are maintained as recommended by vendor. The cells are harvested, washed, and resuspended in a 1:1 mixture of serum free media and Matrigel (354234, Becton Dickinson). The cells are then implanted into athymic nude female mice (Harlan Laboratories) subcutaneously in rear flank at $5\times10^6$ cells/mouse. Tumor volume is estimated by using the formula: $v=l\times w2\times 0.536$ where l=larger measured diameter and w=smaller of perpendicular diameter. The data is analyzed with SAS software (SAS Institutes Inc, Cary, N.C.).

When the mean tumor volume reached 150 mm$^3$ in nude mice, animals are randomized by tumor volume and testing compound is administered in the formulation using vehicle of 20% hydroxypropyl beta cyclodextrin (HPBCD)/25 mM phosphate buffer pH8, with final pH adjusted to pH 9 with 1N NaOH. Ten animals are used per vehicle and treatment groups. For each time point taken, treatment groups are compared to the control vehicle group. Tumor volumes are given as means together with standard errors for each treatment group.

A compound within the scope of the invention is tested in this assay substantially as described above. The compound of Example 1 demonstrates significant anti-tumor growth efficacy in small cell lung cancer NCI-H446 xenograft nude mice model and in small cell lung cancer NCI-H69 xenograft nude mice model.

TABLE 4

Inhibition of SCLC H446 xenograft tumor growth in vivo with Example 1 treatment

| Dosing schedules | Tumor volume Mean (mm$^3$) | Tumor volume SE (mm$^3$) | p-value | Delta T/C (%) | Regression (%) |
|---|---|---|---|---|---|
| vehicle | 698.61 | 319.434 | NA | NA | NA |
| Example 1 30 mg/kg; BID × 21 | 106.19 | 22.729 | <.001* | NA | −45.8 |
| Example 1 50 mg/kg; BID × 21 | 31.62 | 4.340 | <.001* | NA | −83.9 |

Analysis for Tumor Volume is based on Log 10 and SpatialPower covariance structure.
*Significant (p < 0.05); NA: Not Applicable.
Delta T/C (%) is calculated at day30 when the tumor volume in a treated group is at or above baseline tumor volume (day16). The formula is 100 * (T − T0)/(C − C0) where T and C are mean endpoint tumor volume in the treated or control groups, respectively. T0 and C0 are mean baseline tumor volume in these groups.
Regression (%) is calculated when the endpoint volume is below baseline. The formula is 100 * (T − T0)/T0 where T0 are mean baseline tumor volume in the treated groups.

TABLE 5

Inhibition of SCLC H69 xenograft tumor growth in vivo with Example 1 treatment

| Dosing schedules | Tumor volume Mean (mm$^3$) | Tumor volume SE (mm$^3$) | p-value | Delta T/C (%) | Regression (%) |
|---|---|---|---|---|---|
| vehicle | 687.61 | 95.175 | NA | NA | NA |
| Example 1 30 mg/kg; BID × 14 | 73.35 | 9.269 | <.001* | NA | −63.6 |
| Example 1 50 mg/kg; BID × 14 | 72.32 | 8.035 | <.001* | NA | −63.1 |

Analysis for Tumor Volume is based on Log 10 and SpatialPower covariance structure.
*Significant (p < 0.05); NA: Not Applicable.
Delta T/C (%) is calculated at day30 when the tumor volume in a treated group is at or above baseline tumor volume (day16). The formula is 100 * (T − T0)/(C − C0) where T and C are mean endpoint tumor volume in the treated or control groups, respectively. T0 and C0 are mean baseline tumor volume in these groups.
Regression (%) is calculated when the endpoint volume is below baseline. The formula is 100 * (T − T0)/T0 where T0 are mean baseline tumor volume in the treated groups.

I claim:

1. A method of treating small cell lung cancer, comprising administering to a patient in need thereof, an effective amount of a compound selected from the group consisting of:

(2S,4S)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid;

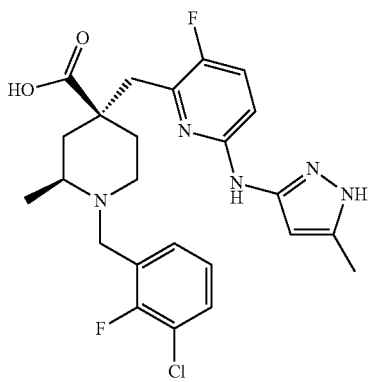

or a pharmaceutically acceptable salt thereof, and (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:

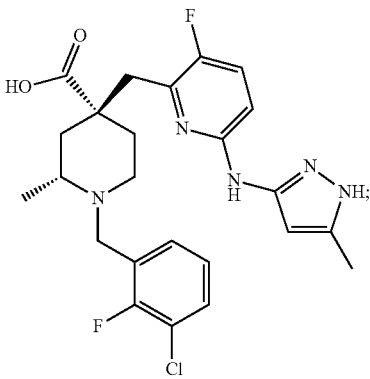

or a pharmaceutically acceptable salt thereof.

2. The method according to claim 1 comprising the compound which is (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:

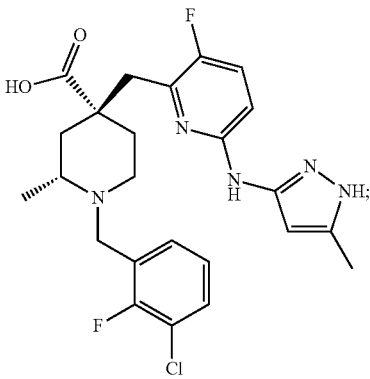

or a pharmaceutically acceptable salt thereof.

3. The method according to claim 1 comprising the compound which is which is (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:

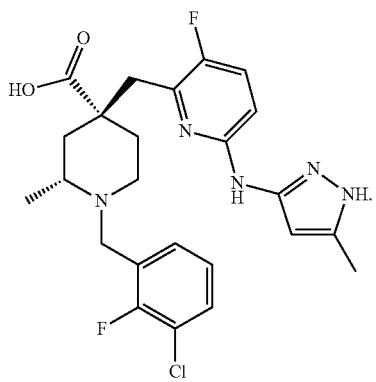

4. A method of treating triple-negative breast cancer, comprising administering to a patient in need thereof, an effective amount of a compound selected from the group consisting of:

(2S,4S)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:

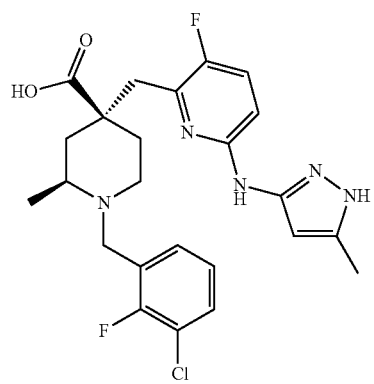

or a pharmaceutically acceptable salt thereof, and (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:

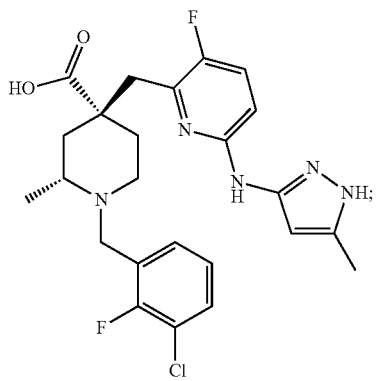

5. The method according to claim 4 comprising the compound which is (2R,4R)-1-[(3-chloro-2-fluoro-phenyl)

methyl]-4-[[3-fluoro-6-[(5-methyl-1H-pyrazol-3-yl)amino]-2-pyridyl]methyl]-2-methyl-piperidine-4-carboxylic acid:
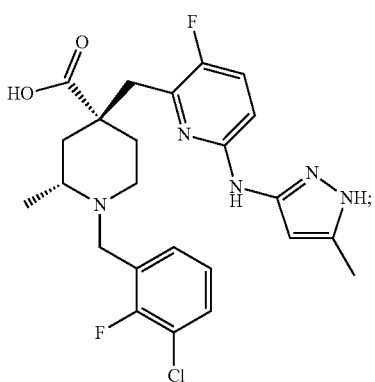
or a pharmaceutically acceptable salt thereof.
6. The method according to claim 4 comprising the compound which is which is (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:
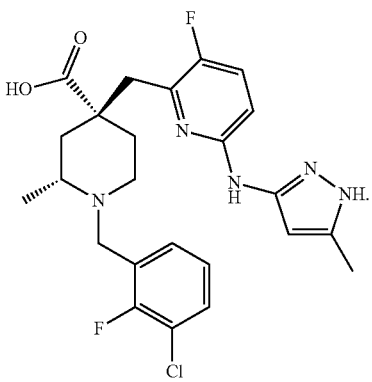
* * * * *

UNITED STATES PATENT AND TRADEMARK OFFICE
CERTIFICATE OF CORRECTION

PATENT NO. : 10,010,540 B2
APPLICATION NO. : 15/407766
DATED : July 3, 2018
INVENTOR(S) : James Robert Henry et al.

It is certified that error appears in the above-identified patent and that said Letters Patent is hereby corrected as shown below:

In the Claims

In Column 25, Line 64, in Claim 3, please delete "which is which is" and insert --which is--, therefore.

In Column 27, Line 22, in Claim 6, please delete "which is which is" and insert --which is--, therefore.

Signed and Sealed this
Eighteenth Day of September, 2018

Andrei Iancu
*Director of the United States Patent and Trademark Office*